United States Patent
Ohashi et al.

(10) Patent No.: US 10,159,909 B2
(45) Date of Patent: Dec. 25, 2018

(54) PARTICLE MANIPULATION METHOD AND PARTICLE MANIPULATION DEVICE

(71) Applicants: SHIMADZU CORPORATION, Kyoto-shi, Kyoto (JP); KAZUSA DNA RESEARCH INSTITUTE, Kisarazu-shi, Chiba (JP)

(72) Inventors: Tetsuo Ohashi, Kyoto (JP); Osamu Ohara, Kisarazu (JP); Ken Nonaka, Kisarazu (JP)

(73) Assignees: SHIMADZU CORPORATION, Kyoto-shi, Kyoto (JP); KAZUSA DNA RESEARCH INSTITUTE, Kisarazu-shi, Chiba (JP)

( * ) Notice: Subject to any disclaimer, the term of this patent is extended or adjusted under 35 U.S.C. 154(b) by 352 days.

(21) Appl. No.: 14/901,791

(22) PCT Filed: Jul. 3, 2013

(86) PCT No.: PCT/JP2013/068250
§ 371 (c)(1),
(2) Date: Dec. 29, 2015

(87) PCT Pub. No.: WO2015/001629
PCT Pub. Date: Jan. 8, 2015

(65) Prior Publication Data
US 2016/0201114 A1    Jul. 14, 2016

(51) Int. Cl.
*B01D 12/00*    (2006.01)
*B01D 15/18*    (2006.01)
(Continued)

(52) U.S. Cl.
CPC ......... *B01D 12/00* (2013.01); *B01D 15/1892* (2013.01); *B03C 1/01* (2013.01);
(Continued)

(58) Field of Classification Search
None
See application file for complete search history.

(56) References Cited

U.S. PATENT DOCUMENTS 4,257,886 A * 3/1981 Kessler ............... B01D 12/00
                                                    206/524.3
5,234,809 A    8/1993 Boom et al.
(Continued)

FOREIGN PATENT DOCUMENTS

JP    2-289596 A    11/1990
JP    2009-162580 A    7/2009
(Continued)

OTHER PUBLICATIONS

International Search Report for PCT/JP2013/068250 dated Aug. 6, 2013.
(Continued)

*Primary Examiner* — Samuel C Woolwine
(74) *Attorney, Agent, or Firm* — Sughrue Mion, PLLC

(57) ABSTRACT

Disclosed is a particle manipulation method including steps of moving particles, which exist in a water-based liquid, into a gelled medium that is insoluble or hardly soluble in the water-based liquid in the water-based liquid, and moving the particles, which exist in the gelled medium, to the outside of the gelled medium. Preferably, the gelled medium is a gel that contains chemically crosslinking polymer. Preferably, the gelled medium has a consistency of 340 to 475. In one embodiment, the movement of the particles existing in the water-based liquid to the gelled medium and the movement of the particles existing inside the gelled medium to the water-based liquid are carried out inside a device, the device being loaded with a plurality of water-based liquids and a gelled medium interposed among the water-based liquids.

14 Claims, 4 Drawing Sheets

(51) Int. Cl.

| | | |
|---|---|---|
| *B03C 1/033* | (2006.01) | |
| *B03C 1/28* | (2006.01) | |
| *C07K 1/14* | (2006.01) | |
| *C12N 15/10* | (2006.01) | |
| *B03C 1/01* | (2006.01) | |
| *C12Q 1/6806* | (2018.01) | |

(52) U.S. Cl.
CPC ............ *B03C 1/0332* (2013.01); *B03C 1/288* (2013.01); *C07K 1/145* (2013.01); *C12N 15/1013* (2013.01); *B03C 2201/26* (2013.01); *C12Q 1/6806* (2013.01)

(56) References Cited

U.S. PATENT DOCUMENTS

| | | |
|---|---|---|
| 2004/0058387 A1 | 3/2004 | Sakurai et al. |
| 2008/0226500 A1 | 9/2008 | Shikida et al. |
| 2012/0135533 A1 | 5/2012 | Shikida et al. |
| 2013/0273552 A1 | 10/2013 | Ohashi |

FOREIGN PATENT DOCUMENTS

| | | |
|---|---|---|
| WO | 02/095407 A1 | 11/2002 |
| WO | 2005/069015 A1 | 7/2005 |
| WO | 2012/086243 A1 | 6/2012 |

OTHER PUBLICATIONS

English translation of Fangzhi Zhuji Huaxue "Textile Auxiliary Chemistry" ISBN 978-7-81111-540-6, 2010 (10 pages total), previously filed May 2, 2017.

* cited by examiner

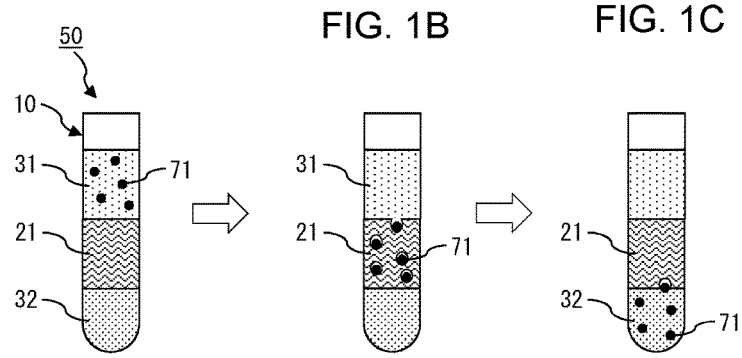
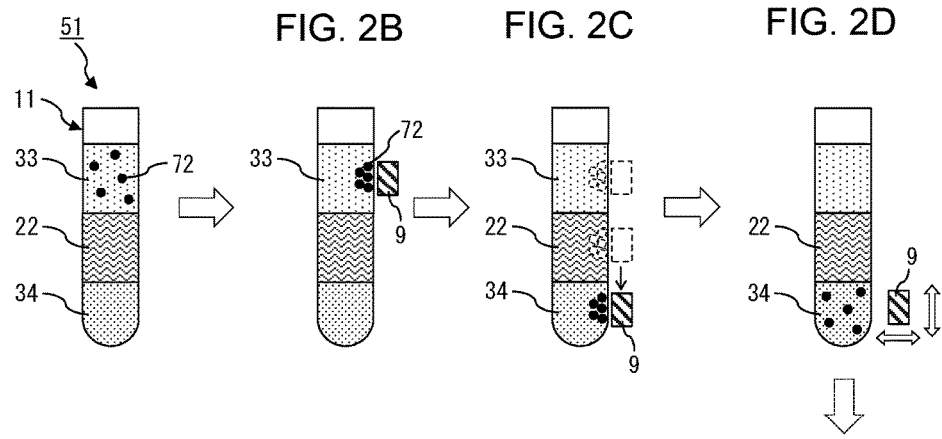
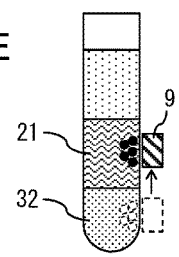

PARTICLE MANIPULATION METHOD AND PARTICLE MANIPULATION DEVICE

CROSS REFERENCE TO RELATED APPLICATIONS

This application is a National Stage of International Application No. PCT/JP2013/068250 filed Jul. 3, 2013, the contents of which are incorporated herein by reference in their entirety.

TECHNICAL FIELD

The present invention relates to a particle manipulation method for performing chemical operations such as separation, extraction, purification and reaction of a target substance, and a manipulation device used therein.

BACKGROUND ART

In medical inspection, management on safety and sanitation of food, monitoring for environmental conservation, and so on, extraction of a target substance from a sample containing a variety of foreign substances is required for detection and reaction of the target substance. For example, in medical inspection, it is necessary to detect, identify and quantitatively determine a nucleic acid, a protein, a sugar, a lipid, a bacterium, a virus, a radioactive substance or the like which is contained in a biological sample separated and acquired from an animal or a plant, such as blood, serum, cells, urine or feces. In these inspections, it may be required to separate and purify a target substance for eliminating adverse effects such as a background ascribable to foreign substances.

For example, in gene examination, a nucleic acid in a biological sample is amplified by a gene amplification method such as PCR (polymerase chain reaction), and a sequence of the nucleic acid is determined. For efficiently amplifying a nucleic acid by a gene amplification method such as PCR, it is necessary that the nucleic acid be extracted and purified from a biological sample containing various foreign substances, and provided for the reaction. In extraction and purification of a nucleic acid in a biological sample, a phenol/chloroform method has been normally used for a long time. However, the phenol/chloroform method has the problem that the operation is complicated, reagents to be used are harmful, and much cost is required for treating a waste liquid.

Patent Document 1 proposes a method for extracting and purifying a nucleic acid from a biological sample by particle manipulation (Boom method), utilizing the nature of a nucleic acid being specifically adsorbed to silica. In this method, first, a solution obtained by treating a sample in the presence of a protease and a surfactant is mixed with silica particles in the presence of a chaotropic substance such as a guanidine salt, an iodide salt or urea to adsorb a nucleic acid to the surfaces of the particles. The silica particles to which the nucleic acid is adsorbed are washed several times for removing foreign substances. Thereafter, the silica particle composite is added in a solution (eluting liquid) having a low salt concentration, so that the purified nucleic acid is eluted in the eluting liquid to obtain a nucleic acid purified sample. Chemical operations applying such particle manipulation are not only targeted at a nucleic acid, but also increasingly applied to, for example, an immunoassay using an antigen-antibody reaction (see, for example, Patent Document 2).

In operations using particles, it is necessary to properly separate particles (solid phase) to which a target sample such as a nucleic acid is adsorbed and a water-based liquid (liquid phase) containing foreign substances which are not adsorbed to the particles. As such a separation operation (B/F separation), a method has been proposed in which a water-based liquid with particles dispersed therein is made to exist as droplets in a liquid immiscible with the water-based liquid (e.g., oil), a nucleic acid or the like is adsorbed to the surfaces of the particles in the water-based liquid droplets, and only particles to which the nucleic acid is adsorbed are then moved into the oil. In addition, a method has been proposed in which particles are moved by magnetic field manipulation using silica-coated magnetic particles or the like for facilitating selective movement of particles.

When a water-based liquid exists as droplets in an oil, the fluid resistance of the oil, the water-repelling force at the interface between the oil and the water-based liquid, the interaction between hydrophilic groups on the surfaces of particles and the water-based liquid, and the like can act as a force for retaining the position and shape of the droplets. Accordingly, when only magnetic particles are to be moved and separated from water-based liquid droplets into an oil, the droplets follow the magnetic field along with the magnetic particles, and therefore it is not easy to separate only particles from the water-based liquid droplets into the oil.

In view of this problem, a method for selectively moving only particles into an oil by suppressing movement of water-based liquid droplets has been proposed. For example, Patent Document 3 discloses a method in which the inner surface of a container, in which droplets and an oil are enclosed, is provided with a physical structure such as a partition wall to block the droplets, and only magnetic particles are moved and separated from a part of a gap. However, in the method disclosed in Patent Document 3, it is necessary to subject the oil enclosing portion to special microprocessing, and therefore the configuration of a device is complicated. Even when a physical structure is provided, the water-based liquid deposited on the peripheries of particles cannot be completely blocked, and therefore B/F separability may not be sufficient.

Patent Document 4 discloses a method in which by applying an electric field to the carrying surfaces of droplets, only magnetic particles are separated with the droplets immobilized at a predetermined position on the carrying surfaces. However, this method has the problem that since droplets cannot be immobilized unless an electric field is constantly applied to a device, the configuration of the device is complicated, and moreover, the method cannot be used in an environment which is short of supply of energy such as electric power. Therefore, the method is not suitable for use in an environment where infrastructure is not fully developed like a developing country or the like, and in an environment where it is required to examine a large number of specimens in a short time, for example, in a state of emergency such as terrorism or disaster. The device to be used in manipulation of a biological sample is preferably disposable for suppression of a problem such as contamination, prevention of infection, and so on. From the above-mentioned viewpoint, it is required to develop a chemical operation method and a device to be used therein that is capable of performing purification, examination and the like conveniently, quickly, at a low cost and in every site.

Patent Document 5 discloses a method in which a low-molecular gelling agent such as a hydroxy fatty acid, a dextrin fatty acid ester or a glycerin fatty acid ester is added to a liquid (silicone oil or the like) immiscible with a water-based liquid to form a physical gel, so that water-based liquid droplets are immobilized at a predetermined position in the oil. The physical gel turns into a sol having fluidity at a temperature higher than the sol-gel transition temperature, and turns into a semi-solid gel having no fluidity at a temperature lower than the sol-gel transition temperature. Accordingly, when the water-based liquid is added in a sol-like oil heated to a temperature equal to or higher than the sol-gel transition temperature, and the oil is then gelled by cooling, water-based liquid droplets are embedded and immobilized in the gel. According to this method, only magnetic particles can be moved into a gel by magnetic field manipulation while water-based liquid droplets are immobilized at a predetermined position in the gel. Accordingly, a water-based liquid containing foreign substances and particles with a target sample immobilized thereon can be conveniently and efficiently separated.

In the method of Patent Document 5, when the oil is heated and thereby solated, the droplets can be released from the embedded and immobilized state to move in the sol-like oil. Thus, the inside of a container, in which the physical gel is enclosed, is given a temperature gradient, so that a region where the oil is in a gel state and a region where the oil is in a sol state coexist, a temperature cycle of PCR can be carried out by performing nucleic acid extraction and purification operations in the low-temperature gel region, and moving particles along with droplets in the oil in the high-temperature sol region. According to this method, extraction and purification of a nucleic acid requiring immobilization of droplets at a predetermined position, and PCR requiring movement of droplets can be performed in one device while a hermetically sealed state is maintained.

PRIOR ART DOCUMENTS

Patent Documents

Patent Document 1: JPA 2-289596
Patent Document 2: WO 2002/095407
Patent Document 3: WO 2005/069015
Patent Document 4: JP A 2009-162580
Patent Document 5: JPA 2011-232260

SUMMARY OF THE INVENTION

Problems to Be Solved by the Invention

In the method disclosed in Patent Document 5, it is necessary that a physical gel be heated and thereby solated, followed by enclosing droplets, and therefore a heating means is required at the time of starting the use of a device. Thus, it is hard to say that the method is suitable for use in an environment which is short of supply of energy such as electric power. For enclosing a gel in a container during preparation of a device, it is necessary to add a gelling agent to an oil, and heat the mixture to a temperature equal to or higher than the sol-gel transition temperature to be admixed, followed by enclosing the mixture in the container while maintaining a sol state, and gelling the mixture in the container. Thus, the gel loading operation is complicated.

Further, the invention disclosed in Patent Document 5 achieves the purpose by using a physical gel that makes a sol-gel transition. However, since the physical gel is solated in a high-temperature environment, it may be unable to achieve the intended purpose of "embedding and immobilizing water-based liquid droplets in a gel to separate the water-based liquid and particles" in a high-temperature environment. The physical gel forms a three-dimensional network by means of a weak intermolecular bonding force such as a hydrogen bond, a Van der Waals force, a hydrophobic interaction or an electrostatic attraction force, and therefore even under a normal-temperature environment, the intermolecular bonding network may be collapsed to form the gel into a sol when an external force such as a shearing force or a pressure is applied to the gel due to, for example, vibration during transportation.

As a result of studies by the inventors, an absorption peak originating from an impurity was found in a nucleic acid solution when a nucleic acid was separated and purified by particle manipulation using a physical gel. Such an impurity may cause a high background in measurement data in analysis operations such as detection, identification and quantitative determination of a target, leading to problems such as a reduction in analysis accuracy and erroneous determination.

In view of these situations, an object of the present invention is to provide a convenient, quick and low-cost particle manipulation method capable of being used independently of an environment, and a device for performing such particle manipulation.

Means for Solving the Problems

As a result of studies conducted by the inventors regarding ingress of foreign substances in particle manipulation using a physical gel as described above, it has been supposed that the foreign substances are derived from a liquid entering from a different liquid fractions via a perforation formed in penetration of particles through a gel, and constituent components of the gel. On the other hand, it has been found that when a chemical gel is used as a gel medium, the gel loading operation is easy, and also, the problem of ingress of foreign substances as caused in the case of using a physical gel is eliminated.

The present invention relates to a particle manipulation method. The particle manipulation method according to the present invention includes the steps of moving particles, which exist in a water-based liquid, into a gelled medium that is insoluble or hardly soluble in the water-based liquid; and moving the particles, which exist in the gelled medium, to the outside of the gelled medium. In a preferred embodiment, movement of the particles to the outside of the gelled medium is movement of particles into a water-based liquid different from the water-based liquid in which the particles are initially contained.

The particle manipulation is performed in, for example, a device loaded with a plurality of water-based liquids with a gelled medium interposed among the water-based liquids. Preferably, the step of moving particles, which exist in a water-based liquid, into a gelled medium, and the step of moving the particles, which exist in the gelled medium, into a different water-based liquid are carried out two or more times in the device. In one embodiment, at least two of a plurality of water-based liquids in the device have mutually different compositions. In this embodiment, a plurality of chemical operations (separation, extraction, purification, reaction and so on) can be performed in one device.

The gelled medium is preferably a gel containing a chemically crosslinked polymer. For example, a silicone gel containing a crosslinked organopolysiloxane is suitably used. The consistency of the gelled medium is preferably 340 to 475. In one embodiment, the gelled medium further contains an oil solution.

In the particle manipulation method according to the present invention, it is preferred that the water-based liquid associated with particles is separated from the particles in movement of the particles into the gelled medium from the water-based liquid and in movement of the particles in the gelled medium.

Particles for use in the present invention are preferably capable of selectively immobilizing a specific substance. Examples of the substance that can be selectively immobilized by particles include organism-derived substances such as nucleic acids, proteins, sugars, lipids, antibodies, receptors, antigens, ligands and cells. The "organism-derived substance" is not necessarily derived from a sample taken from an organism, and may also be a substance obtained in vivo (e.g., a nucleic acid amplified by PCR, or the like).

In one embodiment of the present invention, particles to be subjected to particle manipulation are magnetic particles. In this case, it is preferred to move particles by manipulation of a magnetic field.

The particle manipulation according to the present invention can be applied to, for example, extraction of a nucleic acid immobilized on particles, an antigen-antibody reaction on the surfaces of particles, and so on.

The present invention also relates to a device that is suitably used in the above-mentioned particle manipulation. The device according to the present invention includes a water-based liquid, a gelled medium that is insoluble or hardly soluble in the water-based liquid, a container for holding the water-based liquid and the gelled medium, and particles to be moved in the container.

The present invention also relates to a kit for preparing the device. The device preparing kit according to the present invention includes a water-based liquid, a gelled medium and particles. The kit may be one in which the container is loaded with a part of the above-mentioned constituent elements beforehand.

Effects of the Invention

In the particle manipulation method according to the present invention, particles with a target substance immobilized thereon are brought into contact with a specific gel or caused to pass through the inside of the gel, so that a water-based liquid associated with the particles is separated from the particles while the state in which the target substance is immobilized on the particles is maintained. Accordingly, B/F separation can be performed conveniently, quickly and at a low cost. Gel-derived foreign substances are hardly generated, and therefore adverse effects such as a background caused by foreign substances are eliminated. Accordingly, chemical operations such as separation and purification of a target substance, and reaction can be accurately and efficiently performed. According to the method of the present invention, a plurality of chemical operations can be performed in a closed system within one device without opening and closing a container loaded with a gel and a water-based liquid. Accordingly, the operation is simple and easy, and adverse effects such as contamination can be eliminated.

BRIEF DESCRIPTION OF THE DRAWINGS

FIGS. 1A, 1B, and 1C schematically show the outline of a particle manipulation method according to the present invention.

FIGS. 2A, 2B, 2C, 2D, and 2E schematically show an embodiment in which particles are moved by magnetic field manipulation.

MODE FOR CARRYING OUT THE INVENTION

Figure 3A:
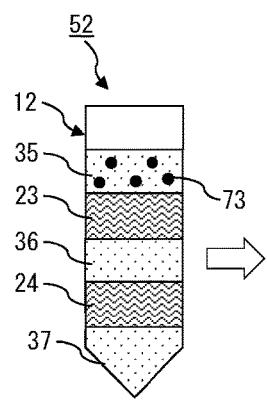
FIGS. 3A, 3B, 3C, 3D, and 3E schematically show a device for moving particles by a centrifugal force, and an embodiment of particle manipulation.

First, the outline and principle of a particle manipulation method according to the present invention will be described.

FIGS. 1A, 1B, and 1C show schematic views for explaining one embodiment of a device 50 to be used in particle manipulation according to the present invention, and a particle manipulation method using the device. In FIG. 1A, a container 10 is loaded with a second water-based liquid 32, a gelled medium 21 and a first water-based liquid 31 in this order from the bottom side. The gelled medium 21 is immiscible with the first water-based liquid 31 and the second water-based liquid 32, and insoluble or hardly soluble in these water-based liquids.

The first water-based liquid 31 contains particles 71. A target substance such as a nucleic acid is immobilized on the surfaces of the particles 71 or in the particles 71. Immobilization of the target substance on the particles 71 is performed in, for example, the first water-based liquid 31. The particles 71 with the target substance immobilized on the surfaces thereof beforehand may be added in the first water-based liquid. The first water-based liquid 31 containing the particles 71 with the target substance immobilized on the surfaces thereof may be injected onto the gelled medium 21 from the opening of the container 10 loaded with the second water-based liquid 32 and the gel 21.

The particles 71 are moved from the first water-based liquid 31 to the gelled medium 21 side under the action of a magnetic field, a gravitational field or the like (FIG. 1B). Most of the water-based liquid physically deposited on the periphery of the particles 71 as droplets is desorbed from the surfaces of the particles and remains in a liquid fraction of the first water-based liquid 31 at the time when the particles 71 enter from the surface to the inside of the gelled medium 21. On the other hand, the particles 71 can easily move in the gelled medium 21 while the target substance stays immobilized on the particles.

When the particles 71 are magnetic particles, and the particles are moved from the first water-based liquid 31 to the gelled medium 21 side by magnetic field manipulation, the particles move in the form of a lump, and thus water-based liquid droplets may remain in the lump. Even when the water-based liquid moves into the gelled medium 21 in association with the particles 71 in this way, droplets of the water-based liquid have a larger volume as compared to individual particles, and therefore cannot move in the gel in association with the particles 71. The restoring force of the gel in passage of the particles 71 through the inside of the gelled medium 21 acts to squeeze the water-based liquid associated with the particles 71. Accordingly, the particles 71 and the water-based liquid droplets associated therewith are separated in the gelled medium 21.

Even when the gelled medium is perforated due to entry and movement of the particles 71 into the gelled medium 21, the holes of the gelled medium 21 are immediately closed under the self-recovery action by the restoring force of the gel. Accordingly, the water-based liquid hardly flows into the gel through the through-holes of the particles.

The particles 71 having passed through the inside of the gelled medium 21 are moved from the gelled medium 21 to the second water-based liquid 32 (FIG. 1C). At this time, even when droplets from the first water-based liquid are associated with the particles 71, the particles 71 come into contact with the second water-based liquid earlier than the droplets. At this time, the first water-based liquid-derived droplets associated with the surfaces of the particles are immediately replaced by the second water-based liquid, and the first water-based liquid-derived droplets remain in the gelled medium. Accordingly, ingress of the first water-based liquid-derived droplets into the second water-based liquid 32 is prevented.

In this way, in the particle manipulation method according to the present invention, the particles 71 existing in the first water-based liquid 31 are moved to the inside of the gelled medium 21, and then moved to the outside of the gelled medium (into the second water-based liquid 32 in the above-mentioned example). By this manipulation, the first water-based liquid droplets associated with the periphery of the particles 71 are removed while the state in which the target substance is immobilized by the particles 71 is maintained. By causing particles to pass through the inside of a gelled medium in this way, a target substance immobilized on solid particles (Bind), and substances unimmobilized on particles such as foreign substances (Free) in the first water-based liquid are appropriately separated, and thus B/F separation is made possible.

According to the above-mentioned method, the gelled medium 21 having no fluidity (or low fluidity) exists between the first water-based liquid 31 and the second water-based liquid 32, and therefore even when particles are moved by a magnetic field or a gravitational field, movement of the water-based liquid into the gelled medium hardly occurs. Accordingly, it is not necessary to perform control of an electric field or the like for preventing inadvertent movement of the water-based liquid, and thus B/F separation is made possible with a simple and easy mechanism. Therefore, washing and liquid replacement of the solid phase surface in a solid phase extraction method can be quickly performed.

In the case where a chemical reaction between a liquid phase and a solid phase is carried out with the particles 71 as the solid phase and the second water-based liquid 32 as the liquid phase, movement of the particles 71 into the second water-based liquid 32 causes the surface of the liquid to be replaced by a solution containing a reactive substrate, a catalyst and other components required for the reaction, so that the reaction can be quickly started. Further, particles pass through the gelled medium 21 to remove most of the first water-based liquid-derived droplets from the surfaces of the particles, and therefore generation of non-target substances by minor reactions or the like is suppressed, so that the background in detection is reduced.

On the other hand, in the case where a target substance is separated and detected by using a chemical interaction, almost all foreign substances other than the target substance are removed during passage of particles through the gelled medium as long as the target substance is specifically immobilized on the particles. Generation of new foreign substances from the gel itself does not occur, and the target substance can be accurately detected qualitatively and quantitatively.

Hereinafter, an embodiment of the present invention will be described more in detail.

Particle Manipulation

In the present invention, particles with a target substance immobilized thereon can be moved from a liquid into a gelled medium to perform B/F separation. Particles in the gelled medium can be moved to a different liquid to perform chemical operations such as extraction, purification, reaction, separation, detection and qualitative/quantitative analysis of the target substance. The particle manipulation is applicable to a pre-treatment performed prior to various kinds of analyses, a target substance isolation (separation) treatment, a dissolving treatment, a mixing treatment, a dilution treatment, a stirring treatment, a temperature control (heating or cooling) treatment and so on.

Examples of the reaction include biological reactions involving transformation of a biological substance, such as enzyme reactions and immunochemical reactions in addition to inorganic chemical reactions and organic chemical reactions. Examples of the biological reaction include synthetic, metabolic and immunological reactions of biological substances such as nucleic acids, proteins, lipids and sugars. The target substance to be subjected to reaction and analysis is not limited to a chemical substance or a biological substance, and a nuclear substance, a radiochemical substance or the like is also applicable. For example, by particle manipulation according to the present invention, reactions for nuclear fission, nuclear fusion, generation of an activation substance, and the like, and analyses for quantitative determination of a radioactive substance, identification of a nuclear species and the like can also be performed.

Particles

Particles for use in the present invention can be subjected to operations such as aggregation, dispersion and movement in a liquid or a gelled medium under the action of a magnetic field, an electric field, a gravitational field, an ultrasonic field or the like. Particles may be solid or semi-solid, and cells of animals and plants and microorganisms may also be handled as particles. For facilitating particle manipulation in a liquid and a gelled medium, the particle size is preferably 1 mm or less, more preferably 0.1 µm to 500 µm. The shape of the particle is desired to be a spherical shape with the particle size being uniform, but may be an irregular shape, and have a measurable particle size distribution as long as particle manipulation is possible. The constituent of the particle may be a single substance, or may include a plurality of components.

Particles for use in the present invention are preferably capable of immobilizing a target substance. The immobilization method is not particularly limited as long as a target substance can be held on the surfaces of particles or in particles, and various kinds of known immobilization mechanisms such as physical adsorption and chemical adsorption are applicable. A target substance is immobilized on the surfaces of particles or in particles by various intermolecular forces such as, for example, a Van der Waals force, a hydrogen bond, a hydrophobic interaction, an interionic interaction and π-π stacking.

Examples of the target substance that is immobilized by particles include organism-derived substances such as nucleic acids, proteins, sugars, lipids, antibodies, receptors, antigens and ligands, and cells themselves. When the target substance is an organism-derived substance, the target substance may be immobilized on particles, or a substance on the surfaces of particles by molecular recognition or the like. For example, when the target substance is a nucleic acid, the nucleic acid can be specifically adsorbed to the surfaces of particles by using silica particles, or particles coated with silica. When the target substance is an antibody (e.g., labeled antibody), a receptor, an antigen a ligand or the like, the target substance can be selectively immobilized on the surfaces of particles by means of amino groups, carboxyl groups, epoxy groups, avidin, biotin, digoxigenin, protein A, protein G or the like on the surfaces of particles.

Magnetic particles are suitably used because aggregation, dispersion and movement can be conveniently and accurately performed by magnetic field manipulation. Examples of the magnetic substance include iron, cobalt, nickel, and compounds, oxides and alloys thereof. Specific examples include magnetite ($Fe_3O_4$), hematite ($Fe_2O_3$ or $\alpha Fe_2O_3$), maghemite ($\gamma Fe_2O_3$), titanomagnetite ($xFe_2TiO_4$-(1-x) $Fe_3O_4$), ilmenohematite ($xFeTiO_3 \cdot (1-x)Fe_2O_3$), pyrrhotite ($Fe_{1-x}S$ (x=0 to 0.13) ... $Fe_7S_8$ (x≈0.13)), greigite ($Fe_3S_4$), geothite ($\alpha FeOOH$), chromium oxide ($CrO_2$), permalloy, alconi magnets, stainless steel, samarium magnets, neodymium magnets and barium magnets.

As magnetic particles, those in which a substance for specifically immobilizing a target substance is deposited on the surface of the magnetic substance, or the surface of the magnetic substance is coated with the above-mentioned substance are suitably used. Examples of the above-mentioned substance for specifically immobilizing a target substance include a compound having various kinds of functional groups, silica, streptavidin, *Staphylococcus aureus*, protein A, protein G, immunoglobulin or the like. As these magnetic particles, commercial products such as Dynabeads (registered trademark) available from Life Technologies, Inc. and MagExtractor (registered trademark) available from TOYOBO CO., LTD. can also be used.

Gelled Medium

The gelled medium for use in the present invention is a semi-solid material which maintains a gel state via a covalent bond. The gel material that forms the gelled medium is in the form of a gel or a paste at least before particle manipulation, and is insoluble or hardly soluble in a water-based liquid to be used.

Gels are classified broadly into physical gels and chemical gels. The physical gel forms a three-dimensional network by means of weak intermolecular bonding forces such as hydrogen bond, Van der Waals force, hydrophobic interaction or electrostatic attraction force, and reversibly makes a sol-gel transition when given an external stimulus such as heat. When a gelled substance is solated, the position of a water-based liquid is not fixed because the sol has fluidity, and thus the water-based liquid moves with movement of particles. Therefore, the physical gel is unsuitable for use in the present invention. When particles pass through the physical gel, the particles move while collapsing the three-dimensional network of the gel. Accordingly, solation easily occurs locally at a part where the gel passes, so that gel-derived foreign substances or the like may be deposited on the surfaces of particles, and taken to the outside of the gel.

On the other hand, the chemical gel is one in which polymer chains are crosslinked via covalent bonds by chemical reaction, and a gel state can be retained as long as a crosslinked structure is maintained. Therefore, the gelled substance for use in the present invention is preferably a chemical gel containing a chemically crosslinked polymer. When particles pass through the chemical gel, the gel is temporarily perforated, but is immediately restored by the restoring force of the gel as described above, and therefore ingress of gel-derived foreign substances or the like is inhibited. In a topological gel (slide-ring polymer), the crosslinking point of which is movable, the crosslinking position may change, but a gel state is retained without collapse of crosslinking before and after particles pass through the gel. Therefore, in this specification, the topological gel is also included in the chemical gel.

In the present invention, the consistency of the gelled medium is preferably 340 to 475, more preferably 355 to 460. The consistency is determined by a mixing consistency test as defined in JIS K2220:2003. In this specification, the consistency refers to a mixing consistency at 25° C. unless otherwise specified. The consistency is an index indicating an apparent hardness of a gelled or paste-like (semi) solid substance, and is represented by a numerical value obtained in the following manner: a depth to which a specified cone penetrates into a sample is measured in the unit of mm, and multiplied by 10. Larger the consistency is (i.e., the deeper the specified cone penetrates), softer the sample is. The consistency ranging from 340 to 475 corresponds to No. 0 to No. 000 in the NLGI consistency number defined by National Lubricating Grease Institute.

When the consistency of the gelled medium is 475 or less, the gel has low fluidity, and therefore separation of droplets associated with the surfaces of particles is accelerated by the restoring force of the gel when the particles move in the gel. When the consistency of the gelled medium is 360 or more, the gel has moderate fluidity, and therefore under the action of a magnetic field, a gravitational field or the like, particles can be forced into the gel from the water-based liquid, and moved in the gel.

Preferably, the gelled medium for use in the present invention has a small temperature dependency of the consistency. For example, the consistency of the gelled medium is preferably in the above-mentioned range even when the gelled medium is heated to 60° C. When the temperature dependency of the consistency is small, particle manipulation can be appropriately performed without depending on the use environment. Also from such a viewpoint, it is preferred that a chemical gel is used as the gelled medium according to the present invention, as described above.

As the gelled medium, a silicone gel, for example, is suitably used. Examples of the polymer that forms a silicone gel include crosslinked organopolysiloxanes such as crosslinked organopolysiloxanes, alkyl-modified partially crosslinked organopolysiloxanes and silicone branched alkyl-modified partially crosslinked organopolysiloxanes. Dimethicone, vinyldimethicone, methyl trimethicone, methylvinylsiloxane, lauryl dimethicone, a copolymer thereof or the like may be used as the organopolysiloxane. The molecular structure of the polymer is not particularly limited, and may be a linear structure, a branched linear structure, a cyclic structure or a network structure.

Preferably, the silicone gel contains an oil solution in addition to the above-mentioned polymer. As the oil solution, a solvent that swells the polymer and is immiscible with the water-based liquid is suitably used. Examples of the above-mentioned solvent include cyclopentasiloxane, cyclomethicone, dimethicone, dimethiconol, methyl trimethicone, phenyl trimethicone, cyclopentasiloxane, diphenyl siloxy phenyl trimethicone, mineral oil, isododecane, isodecyl neopentanoate, trioctanoin and squalane. For example, the polymer is micronized, and mixed with an oil solution to obtain a gelled or paste-like silicone gel.

The content of the polymer in the gelled medium is appropriately set according to the molecular weight, the crosslinking degree or the like of the polymer so that the gelled medium has a moderate consistency. The content of the polymer in the gelled medium is, for example, 0.01 to 100% by weight, preferably 0.1 to 90% by weight, more preferably 0.5 to 85% by weight. As the gelled medium, a commercial product of a silicone gel with a polymer and an oil solution mixed beforehand can also be used. Such a commercial product can be acquired from, for example, Shin-Etsu Chemical Co., Ltd. and Dow Corning.

The gelled medium for use in the present invention is not limited to a silicone gel as long as it is a substance insoluble or hardly soluble in the water-based liquid, and various kinds of gel materials can be used. As described above, the gel material is preferably a chemical gel. Preferably, the gel material has a consistency of 340 to 475. Preferably, the gel material has a high kinetic viscosity and low fluidity, and for example, the kinetic viscosity at 25° C. is preferably 50 $mm^2/cm$ or more.

As the gel material that can satisfy the above-mentioned requirement, hydrocarbon-based gels such as those of polyethylene, polystyrene, polypropylene, polyvinyl chloride and (meth)acrylic polymers; silicone-based gels such as those of polysiloxane, PDMS and silicone hydrogels; fluorine-based gels such as PTFE, PFA, FEP, ETFE and PCTFE; gelled or paste-like mixtures mainly composed of these materials; and the like can also be used. Specific examples of the hydrocarbon-based gel include Plastibase (registered trademark) which is mainly composed of polyethylene.

Water-Based Liquid

The water-based liquid provides a field for chemical operations such as extraction, purification, reaction, separation, detection and analysis of a target substance immobilized on the surfaces of particles. The water-based liquid can serve as a mere medium for these chemical operations, and may also be directly involved in the chemical operation, or contain as a component a compound which is involved in the operation. Examples of the substance contained in the water-based liquid may include substances that react with a reactive substance immobilized on particles, substances that further react with a substance immobilized on the surfaces of particles by the reaction, reaction reagents, fluorescent substances, various kinds of buffers, surfactants, salts, various kinds of other auxiliary agents, and organic solvents such as alcohols. The water-based liquid can be provided in any form such as water, an aqueous solution or an aqueous suspension. In the case where a plurality of water-based liquids are enclosed in a container with a gelled medium interposed among the water-based liquids, the water-based liquids may be the same or different.

Examples of the water-based liquid will be shown below for the case where a nucleic acid is separated and purified by particle manipulation, and the case where an enzyme immunoreaction is carried out.

Separation and Purification of Nucleic Acid

In the case where a nucleic acid is separated and purified by particle manipulation, it is preferred to use a device loaded with a nucleic acid extraction liquid, a washing liquid and a nucleic acid releasing liquid along the direction of moving particles with gelled media interposed among the liquids (see FIG. 4).

The sample containing a nucleic acid is not particularly limited. Examples thereof may include biological samples such as animal and plant tissues, body fluids and excretions, and nucleic acid inclusion bodies such as cells, protozoa, fungi, bacteria and viruses. The body fluids include blood, spinal fluids, saliva and milk, and the excretions include feces, urine and sweat. A combination of two or more thereof may also be used. The cells include leukocytes and blood platelets in blood, exfoliated cells of mucosal cells such as oral cells, and leukocytes in saliva, and a combination thereof may also be used. The sample containing a nucleic acid may be prepared in the form of a cell suspension, a homogenate, or a mixed liquid with a cell lysate.

Nucleic Acid Extraction Liquid

Examples of the nucleic acid extraction liquid to be used for extracting a nucleic acid include buffers containing a chaotropic substance, EDTA, tris-hydrochloric acid or the like. Examples of the chaotropic substance include guanidine hydrochloride, guanidine isothiocyanate, potassium iodide and urea. In the presence of such a substance, a nucleic acid is specifically adsorbed to the surfaces of silica particles (or silica-coated particles). Accordingly, when the sample containing a nucleic acid and silica particles are added in a nucleic acid extraction liquid, the nucleic acid is selectively immobilized on the surfaces of the particles. A specific method for extracting a nucleic acid from a sample containing the nucleic acid can be appropriately determined. For example, by referring to Japanese Patent Laid-open Publication No. 2-289596, extraction and purification of a nucleic acid from a sample containing the nucleic acid can be performed using magnetic particles.

Washing Liquid

The washing liquid is not limited as long as it ensures that components other than a nucleic acid (e.g., proteins, sugars and so on), which are contained in a sample, and a reagent or the like used for a treatment such as nucleic acid extraction can be released into the washing liquid. Examples of the washing liquid include high-salt-concentration aqueous solutions such as those of sodium chloride, potassium chloride and ammonium sulfate, and aqueous alcohol solutions such as those of ethanol and isopropanol.

A person skilled in the art can appropriately determine a method for washing particles with a nucleic acid immobilized thereon. Washing with two or more washing liquids can also be performed depending on the type of sample, purpose of separation, application, or the like. On the other hand, washing may be omitted as long as undesired hindrance in the purpose of separation and application does not occur.

Nucleic Acid Releasing Liquid

As the nucleic acid releasing liquid, water, or a buffer containing a low-concentration salt can be used. Specifically, a tris-buffer, a phosphate buffer, distilled water or the like can be used. Particularly, a 5 to 20 mM tris-buffer adjusted to have a pH of 7 to 9 is generally used. Particles with a nucleic acid immobilized thereon move into the nucleic acid releasing liquid, so that the nucleic acid can be released from the surfaces of the particles. Specific examples of the method for eluting a nucleic acid from particles with the nucleic acid immobilized thereon include a method in which particles are suspended in the eluting liquid. Elution conditions such as the suspension method, stirring time for suspension and temperature during elution can be appropriately determined so as to increase the nucleic acid collection amount.

ELISA Method

In the case where an enzyme-linked immuno-sorbent assay is carried out by particle manipulation, for example, a device can be used in which a container is filled with a first water-based liquid, a second water-based liquid, a third water-based liquid, a fourth water-based liquid and a fifth water-based liquid along the direction of moving particles with a gelled medium interposed among the liquids.

In this case, the particles are sequentially moved from the first water-based liquid side to the fifth water-based liquid. An antigen reaction between a primary antibody immobilized on the surfaces of the particles and a test antigen (test substance) in the sample is carried out in the first water-based liquid; a washing treatment is performed in the second water-based liquid; an antigen-antibody reaction between an enzyme labeled secondary antibody and the test antigen is carried out in the third water-based liquid; a washing treatment is performed again in the fourth liquid; and a coloring reaction between an enzyme bonded to the secondary antibody immobilized on the surfaces of the particles and a coloring substance contained in the water-based liquid is carried out in the fifth water-based liquid for a fixed time. In the ELISA method, a coloring reaction using a coloring substance is carried out as described above, and therefore the antigen-antibody reaction is made visible.

Further, as necessary, the particles may be moved to a sixth water-based liquid to perform an additional treatment (e.g., mixing), followed by measuring the result of the reaction in the fifth water-based liquid. The result of the reaction in the fifth water-based liquid can be quantitatively evaluated by absorbance measurement using a spectrophotometer. As for qualitative evaluation, the coloring reaction may be visually examined.

In the case where quantitative analysis is performed by a conventional ELISA method, it is necessary to stop the coloring reaction by adding a reaction stopping reagent such as sodium hydroxide at the time of elapse of a predetermined time after the start of the coloring reaction. In contrast, according to the above-mentioned method, the reaction can be stopped by moving particles to the outside of the system of the fifth water-based liquid, and therefore the result of the reaction can be conveniently obtained in the closed system without adding a reaction stopping reagent.

For the composition of each water-based liquid to be used in the ELISA method, one suitable for each treatment can be appropriately selected by a person skilled in the art. Some of the operations may be performed outside the device, followed by performing the other operations by particle manipulation, or some of the operations may be performed by particle manipulation, followed by performing the other operations outside the device.

The example of performing separation and extraction of a nucleic acid in the device and the example of carrying out the ELISA method have been described above, and by using appropriate water-based liquids, chemical operations other than those described above, such as extraction, purification, reaction, separation, detection and analysis can be performed in one device.

Container

The above-mentioned gelled medium and water-based liquids are enclosed in a container in their use. The material and shape of the container are not particularly limited as long as it is capable of holding gelled medium and water-based liquids. For example, a straight-tubular structure (capillary) having an inner diameter of about 1 to 2 mm and a length of about 50 mm to 200 mm, a structure with a flat plate material bonded to the upper surface of a different flat plate material provided with a linear groove having a width of about 1 to 2 mm, a depth of about 0.5 to 1 mm and a length of about 50 mm to 200 mm, or the like is used.

By reducing the size of the container as much as possible, the device can be used as a micro-device for minute liquid manipulation, or a chip for minute liquid manipulation. The shape of the container is not limited to a tubular shape or a planar shape, and the particle movement passage may have a branched structure such as a cross shape or a T shape. A conical container such as an Eppendorf tube may also be used.

In the present invention, particles in a container can be moved by manipulation of a magnetic field, a gravitational field or the like, and therefore the container can be brought into a closed system after a sample being introduced. When the container is brought into a closed system, contamination from outside can be prevented. Accordingly, the closed system is particularly useful when an easily decomposable substance such as an RNA is manipulated. For bringing the container into a closed system, the opening of the container can be heat-sealed, or the container can be sealed using an appropriate sealing means. In the case where it is necessary to take manipulated particles and a water-based liquid to the outside of the container, it is preferred to detachably seal the opening using a resin stopper or the like.

When magnetic particles are to be moved by magnetic field manipulation, a magnet is moved along the outer wall surface of the container. This manipulation causes the magnetic particles to follow the magnet and move along the inner wall surface of the container. When the inner wall surface of the container provides a particle carrying surface in this way, the inner wall surface of the container is preferably smooth for reducing the frictional resistance in carriage of the particles. For example, the arithmetic mean surface roughness Ra of the inner wall surface is preferably 0.1 μm or less. Preferably, the inner wall surface of the container has water repellency. When the inner wall surface of the container is water-repellent, the frictional resistance in carriage of particles is reduced, and separation of a water-based liquid from particles can be accelerated. Preferably, the inner wall surface of the container has a water-based liquid contact angle of about 95° to 135° at 25° C.

Examples of the material having the above-mentioned properties include resin materials such as polyolefins such as polypropylene and polyethylene, fluorine-based resins such as tetrafluoroethylene, polyvinyl chloride, polystyrene, polycarbonates and cyclic polyolefins. In addition to these materials, ceramic, glass, silicone, metals and so on may also be used. The inner wall surface of the container may be coated with a fluorine-based resin, silicone or the like for improving the water repellency thereof.

In the case where optical measurement of an absorbance, a fluorescence, a chemiluminescence, a bioluminescence, a change in refractive index, or the like is performed during or after manipulation of particles, or photoirradiation is performed, a container permeable to light is preferably used. In addition, the use of a container permeable to light is preferred because the state of particle manipulation in the container can be visually observed. On the other hand, in the case where it is necessary to shield a water-based liquid, particles and so on from light, a container impermeable to light, such as one made of a metal or the like, is preferably used. A container having a light-permeable part and a light-shielding part may also be employed depending on the use purpose or the like Loading of Gelled Medium and Water-Based Liquid A container can be loaded with a gelled medium and a water-based liquid by an appropriate method. In the case where a tubular container is used, it is preferred that the opening at one end of the container is sealed prior to loading, and the container is loaded with a gelled medium and a water-based liquid sequentially through the opening at the other end. In the case where a capillary-like small structure having an inner diameter of about 1 to 2 mm is loaded with a gelled medium, the loading is performed by, for example, a method in which a metallic injection needle is attached to a Luer lock type syringe, and the gelled medium is extruded to a predetermined position in the capillary.

The volume of each of the gelled medium and the water-based liquid loaded in the container can be appropriately set according to the amount of particles to be manipulated, the type of manipulation or the like. In the case where a plurality of gelled medium regions and water-based liquid regions are provided in the container, the volumes of the regions may be the same or different. The thickness of each region can be appropriately set, but for example, it is preferably about 2 mm to 20 mm in consideration of manipulability or the like.

Particle Manipulation Device and Kit

The container may be loaded with a gelled medium and a water-based liquid immediately before particle manipulation, or after a sufficient time before particle manipulation. Since the gelled medium and the water-based liquid are immiscible with each other as described above, reaction or absorption hardly occurs between the gelled medium and the water-based liquid even after elapse of a long time after loading. The gelled medium for use in the present invention is more stable as compared to a physical gel, and is therefore hardly solated even when placed under the physical action of vibration or the like during conveyance after loading of the gel, or heated in exposure to a high-temperature environment. Accordingly, the particle manipulation device according to the present invention can be provided with a container loaded with a water-based liquid and a gelled medium beforehand. The device can be provided with particles added therein beforehand.

Particles themselves or particles contained in a water-based liquid may be provided independently of a device main body. In this case, particles may be provided as one constituent member of a kit for preparing the device. For example, particles may be included as a constituent element of the kit together with other constituent members such as a container, a gelled medium and a water-based liquid. The kit may be configured in such a manner that a container loaded with a water-based liquid and/or a gelled medium can be further loaded with an additional water-based liquid and/or an additional gelled medium as necessary.

The amount of particles which are contained in the device or the kit is appropriately determined according to the type of intended chemical operation, the volume of each water-based liquid, or the like. For example, in the case where a long and narrow cylindrical capillary having an inner diameter of about 1 to 2 mm is used as the container, the suitable amount of particles is normally in the range of about 10 to 200 µg.

[Particle Manipulation Means]

Manipulation for movement of particles from the water-based liquid to the gelled medium, and manipulation for movement of particles from the gelled medium to the water-based liquid can be performed using various kinds of methods. For example, in the case where magnetic particles are manipulated by a magnetic field, magnetic field manipulation can be performed using a magnetic force source such as a permanent magnet (e.g., ferrite magnet or neodymium magnet) or electric magnet. FIGS. 2A, 2B, 2C, 2D, and 2E schematically show one example of a particle manipulation method using a magnetic field.

In FIG. 2A, particles 72 are dispersed in a first water-based liquid 33. By disposing a magnet 9 as a magnetic force source at the outside of a container, the magnetic particles 72 dispersed in the water-based liquid in a container 11 can be aggregated on the inner wall surface of the container (FIG. 2B). Accordingly, the magnetic force source causes the magnetic particles to generate a magnetic field via the wall surface of the container, so that the magnetic particles can be manipulated to move to an intended position. As shown in FIG. 2C, when the magnet 9 is moved in the longitudinal direction of the container, the aggregate of the magnetic particles follows the movement of the magnetic force source and moves along the inner surface of the tube from the first water-based liquid 33 to a gelled medium 22, and to a second water-based liquid 34 sequentially. After the magnetic particles 72 are moved to the second water-based liquid 34, the magnetic particles 72 can be dispersed in the second water-based liquid 34 by reciprocating the magnet 9 or changing the distance between the magnet 9 and the container 11 (FIG. 2D).

In the case where only the second water-based liquid is collected, or the optical properties of the second water-based liquid are measured, it is preferred to move the magnetic particles to the outside of the region of the second water-based liquid 34. For example, as shown in FIG. 2E, the magnetic particles 72 can be removed to the outside of the region of the second water-based liquid 34 by performing magnetic field manipulation again to move the magnetic particles 72 into the gelled medium 22. FIGS. 2A, 2B, 2C, 2D, and 2E illustrate an example in which the container has two water-based liquid regions therein, and in the case where the container has three or more water-based liquid regions, aggregation and movement of the magnetic particles may be repeated again after the magnetic particles are dispersed in the water-based liquid.

Examples of the method of particle manipulation which does not use a magnetic field include methods using a gravitational field or an electric field. As particle manipulation using a gravitational field, for example, particles can be moved by means of a centrifugal field using a centrifugal machine. In the case where the particles are metal particles such as those of aluminum, the particles can be moved by electromagnetic induction. Alternatively, particle manipulation can be performed by means of ultrasonic vibration as long as the physical properties of the gelled medium and the immobilization state of particles and a target substance are not affected. For performing the manipulation, the particles may be magnetic or non-magnetic.

Figure 3B:
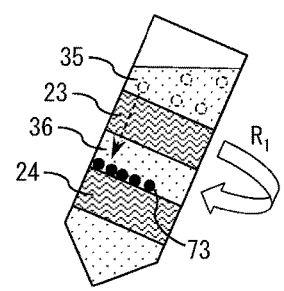
Figure 3C:
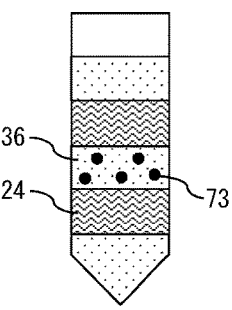
Figures 3D, 3E:
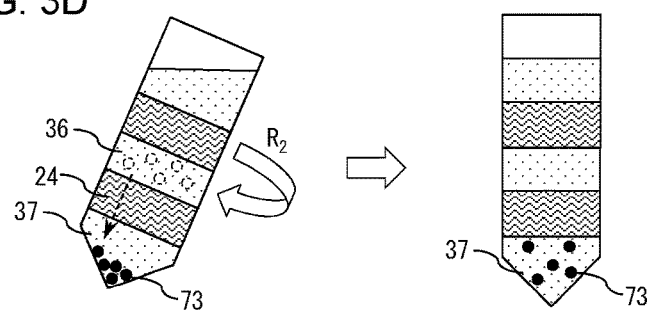

FIGS. 3A, 3B, 3C, 3D, and 3E schematically show one example of a device for performing particle manipulation by means of a gravitational field, and an embodiment of particle manipulation using such a device 52. In FIG. 3A, a third water-based liquid 37, a second gelled medium 24, a second water-based liquid 36, a first gelled medium 23 and a first water-based liquid 35 are layered in this order from the bottom in a container 12. Particles 73 are dispersed in the first water-based liquid. By performing a centrifugal operation with the device 53 rotated at a predetermined rotation number using a centrifugal machine, the particles 73 in the first water-based liquid 35 are moved to the first gelled medium 23, to the second water-based liquid 36, to the second gelled medium 24, and to the third water-based liquid 37 sequentially (FIGS. 3A and 3D). Manipulation for movement of particles can be performed not only by the use of a centrifugal machine, but also by a method in which a gravitational field is applied by shaking the container while the upper part of the container 12 is held.

In the case where the plurality of gelled media 23 and 24 are layered in the container, the container is loaded with the plurality of gelled media in such a manner that the consistency of the gelled medium sequentially decreases from the upper part toward the bottom of the container in one embodiment. For example, in the example illustrated in FIGS. 3A, 3B, 3C, 3D, and 3E, the consistency of the first gelled medium 23 situated on the upper side is larger than the consistency of the second gelled medium 24 situated on the bottom side (the first gelled medium is softer).

In this embodiment, a device can be designed in such a manner that when a first gravitational field is applied, the particles 73 pass through the first gelled medium 23, but do not pass through the second gelled medium 24. In the device after the first gravitational field is applied, the particles 73 remain in the second water-based liquid 36 (FIG. 3B). When the device is shaken in this state, the particles 73 can be dispersed in the second water-based liquid 36 to appropriately perform a chemical operation in the water-based liquid (FIG. 3C).

Thereafter, by giving a second gravitational field greater than the first gravitational field, the particles 73 in the second water-based liquid can be caused to pass through the second gelled medium 24 and move to the third water-based liquid 37 (FIG. 3D). Further, the particles 73 can be dispersed in the third water-based liquid 37 by shaking the device as necessary (FIG. 3E).

Thus, when a plurality of gelled media having different consistencies are used, intended chemical operations can be appropriately performed in a plurality of water-based liquids using a method other than magnetic field manipulation. As a method for adjusting the gravitational field, for example, a rotation number $R_2$ for giving a second centrifugal field may be made larger than a rotation number $R_1$ for giving a first centrifugal field in the case where a centrifugal machine is used.

A device using a centrifugal field as described above may also be used as, for example, a spin column to be used for purification or pretreatment of a sample. Particularly, in the present invention, a chemical gel is used as the gelled medium, and therefore even when operations such as application of an external force such as a centrifugal force and shaking are performed, the three-dimensional network of the gel is retained to maintain a gel state. Accordingly, particle manipulation can be performed without causing a problem such as ingress of gelled medium-derived foreign substances associated with solation as is caused when a physical gel is used.

EXAMPLES

Example 1

In Example 1, genome DNA was extracted from human whole blood using magnetic beads. As magnetic beads, magnetic beads included with a nucleic acid extraction kit (MagExtractor™-Genome) manufactured by TOYOBO CO., LTD. were resuspended in distilled water in such a manner that the concentration was 650 mg/mL, and the suspension thus obtained was used.

<Preparation of Device for Separation and Purification>

Figure 4A:
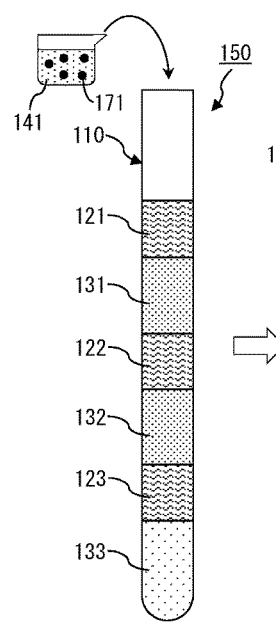
FIGS. 4A, 4B, 4C, 4D, 4E, 4F, 4G, and 4H schematically show a device to be used in separation and purification of a nucleic acid, and an embodiment of particle manipulation in the device.

First, one end of a polypropylene pipe (inner diameter: 2 mm; outer diameter: 3.8 mm; manufactured by Nirei Industry Co., Ltd.) was heated and melted to be sealed, so that a container was formed. This container was loaded with 150 μL of an eluting liquid (distilled water: DNase, RNase free; manufactured by NACALAI TESQUE, INC.), 20 μL of a silicone gel (trade name "KSG-15", manufactured by Shin-Etsu Chemical Co., Ltd.), 150 μL of a second washing liquid (70% ethanol, 10 mM Tris-HCl, 10 mM EDTA, pH 8.0), 20 μL of a silicone gel (KSG-15), 150 μL of a first washing liquid (30% ethanol, 2 M guanidine hydrochloride) and 20 μL of a silicone gel (KSG-15) in this order from the bottom. In this way, a tubular device 150 for separation and purification was obtained, in which a first gelled medium 121, a first washing liquid 131, a second gelled medium 122, a second washing liquid 132, a third gelled medium 123 and an eluting liquid 133 were layered from the opening end side of a container 110, as shown in FIG. 4A. The silicone gel (KSG-15) used here was a physical gel obtained by swelling a crosslinked product of a copolymer of dimethicone and vinyldimethicone with cyclopentasiloxane, and had a consistency of 420 at 25° C.

Cytolysis and Protease Treatment

In a 1.5 mL Eppendorf tube, 200 μL of human stored blood was taken, 100 μL of a cell lysate (4 M GuSCN, 40 mM aqueous Tris-HCl solution, pH 6.5) and 20 mg/mL of an aqueous protease K (manufactured by Roche Applied Science) solution were added, and the mixture was stirred for about 10 seconds by a vortex mixer. Subsequently, the mixture was immediately heated to 68° C., and subjected to an enzyme reaction for 5 minutes. To the liquid after the reaction, 100 μL of isopropyl alcohol and 10 μL of magnetic beads suspension were added, and the mixture was stirred for about 10 seconds by a vortex mixer to adsorb DNA in the cell lysate to the surfaces of the magnetic beads.

<Manipulation for Extraction and Separation of DNA>

Figure 4B:
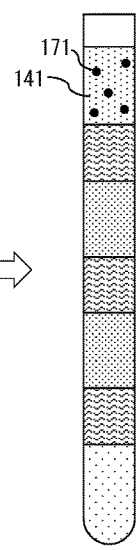

The cell lysate 141 together with magnetic beads 171 were introduced into the device 150 from the upper end opening of the tubular device (FIG. 4B). A neodymium magnet (cylindrical shape with a diameter of 6 mm and a length of 23 mm; trade name "NE127" manufactured by Niroku seisakusho Co., Ltd.) as the magnet 9 was moved so as to trace the side surface of the container 110 at a speed of 0.5 to 5 mm per second toward the lower end bottom of the device 150 in the manner shown in FIGS. 4C, 4D, 4E, and 4F, so that the magnetic beads were manipulated.

Figure 4C:
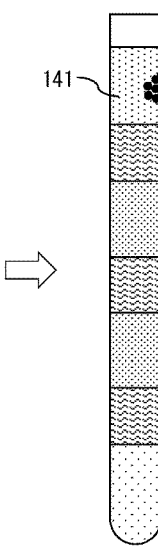
Figure 4D:
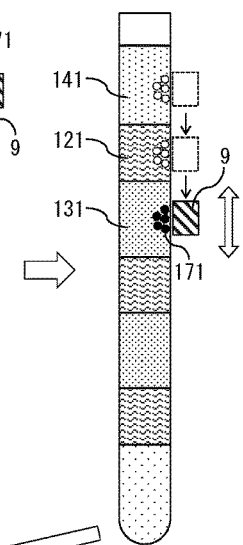

First, the magnet 9 was made close to the side surface of the tubular container 110, so that the magnetic beads 171 in the cell lysate 141 were collected in the vicinity of the magnet 9 (FIG. 4C). The magnet 9 was then moved from the side surface of the cell lysate 141 toward the side surface of the first washing liquid 131. Accordingly, the magnetic beads 171 were moved into the first washing liquid 131 from the cell lysate 141 through the first gelled medium 121 (FIG. 4D). For improving washing efficiency, the magnet 9 was reciprocated to disperse the magnetic beads 171 in the first washing liquid 131.

Figure 4E:
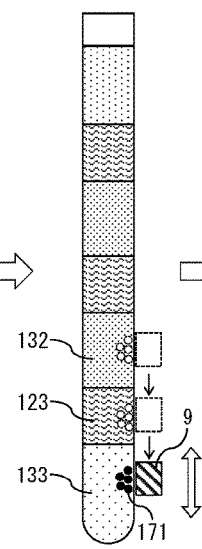
Figure 4F:
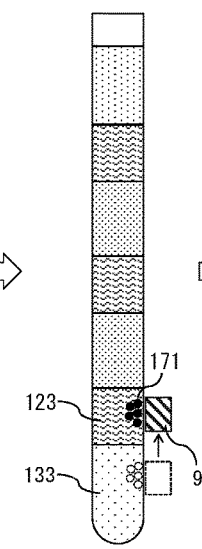

Thereafter, the magnet 9 was moved from the side surface of the first washing liquid 131 toward the side surface of the second washing liquid 132 to move the magnetic beads 171 into the second washing liquid 132 from the first washing liquid 131 through the second gelled medium 122 (FIG. 4E). The magnet 9 was reciprocated to disperse the magnetic beads 171 in the second washing liquid 132, and the magnet 9 was then moved from the side surface of the second washing liquid 132 toward the side surface of the eluting liquid 133 to move the magnetic beads 171 into the eluting liquid 133 from the second washing liquid 132 through the third gelled medium 123 (FIG. 4F).

Figure 4G:
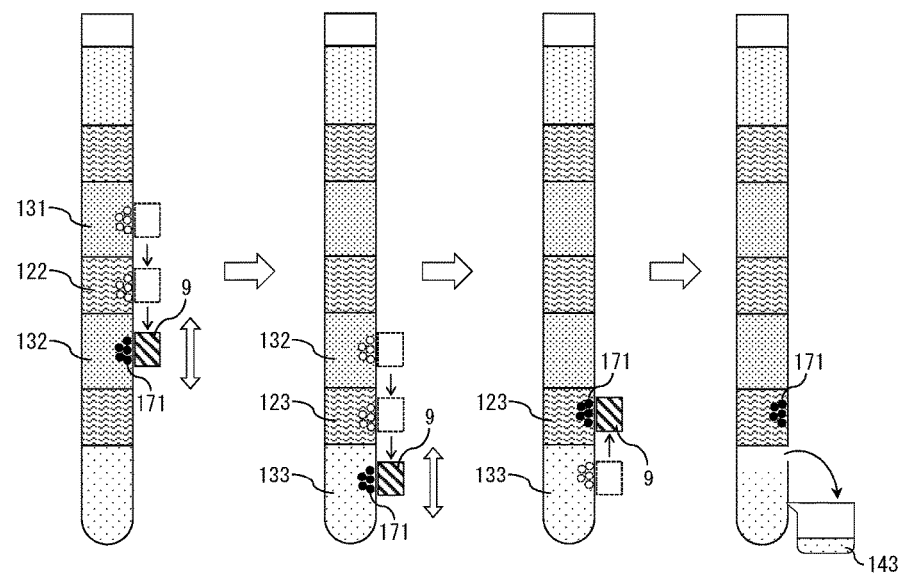
Figure 4H:
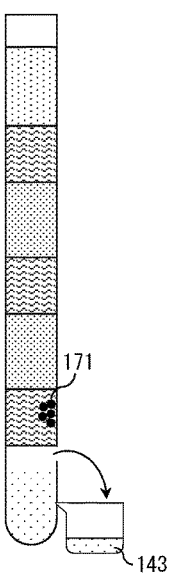

The magnet 9 was reciprocated to disperse the magnetic beads 171 in the eluting liquid 133, so that DNA adsorbed to the magnetic beads was eluted in the eluting liquid (distilled water). Thereafter, the magnet 9 was moved from the side surface of the eluting liquid 133 to the third gelled medium 123, so that the magnetic beads 171, from which DNA had been eluted, were moved to the third gelled medium (FIG. 4G). The surface of the polypropylene tube in the vicinity of the interface of the eluting liquid 133 with the third gelled medium 123 was incised with a cutter knife to break the tube, and a DNA-eluted liquid 143 was collected through the opening (FIG. 4H).

Comparative Example 1

In Comparative Example 1, genome DNA was extracted from human whole blood using magnetic beads in the same manner as in Example 1, but Comparative Example 1 was different from Example 1 in that the gel to be used for separation was changed from a chemical gel to a physical gel.

Preparation of Physical Gel 12-hydroxystearic acid (Wako Pure Chemical Industries, Ltd.) as a gelling agent was added to a silicone oil (KF-56 manufactured by Shin-Etsu Chemical Co., Ltd.) in such a manner that the content of the gelling agent was 1%, and the mixture was heated to 90° C. to completely mix the gelling agent with the silicone oil. Thereafter, the mixture was held with the oil temperature decreased to about 60° C.

Preparation of Device for Separation and Purification

A polypropylene pipe same to that used in Example 1 was loaded with 150 µL of an eluting liquid, 20 µL of a gelling agent-added oil, 150 µL of a second washing liquid, 20 µL of a gelling agent-added oil, 150 µL of a first washing liquid and 20 µL of a gelling agent-added oil in this order from the bottom, and then allowed to cool to room temperature, so that the oils were gelled.

Manipulation for Extraction and Separation of DNA

Using a device loaded with the physical gel, the same magnet manipulation as in Example 1 was performed to extract and separate DNA from human stored blood.

Comparison Between Example 1 and Comparative Example 1

UV absorption spectrum of the eluting liquid collected in each of Example 1 and the comparative example was measured using a spectrophotometer ("BioSpec-nano" manufactured by Shimadzu Corporation). The results are shown in FIG. 5.

Figure 5:
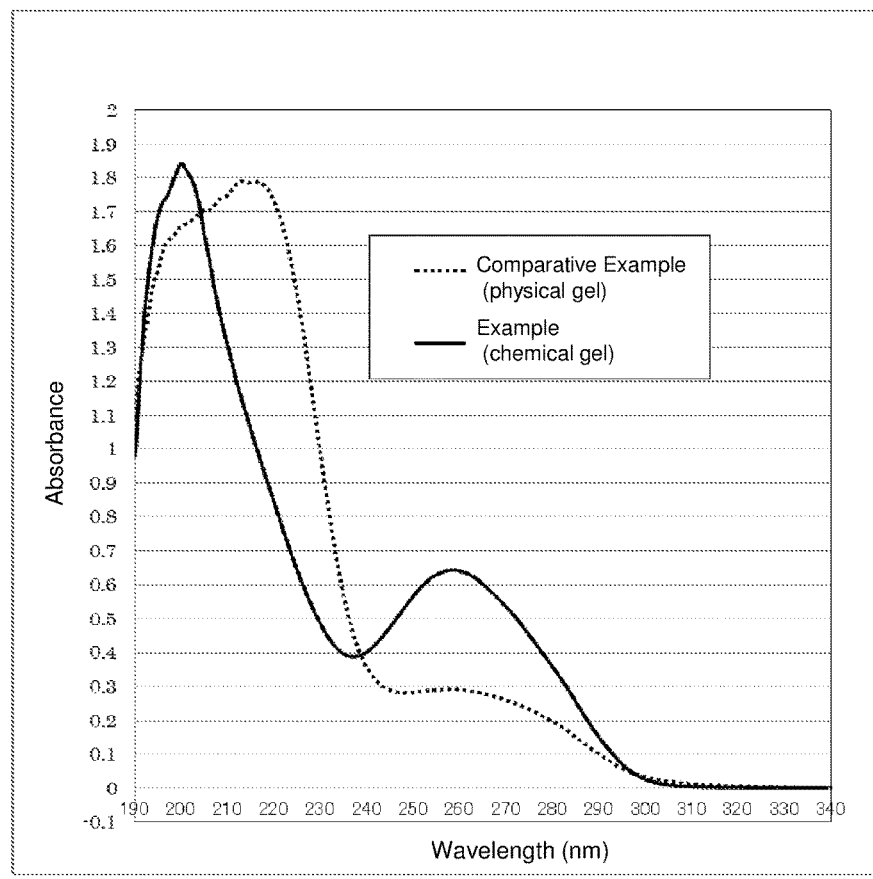
FIG. 5 shows UV absorption spectra of nucleic acids extracted and purified by particle manipulation in the Example and Comparative Example.

As is evident from FIG. 5, an intense absorption was observed around 220 nm in Comparative Example 1 where a physical gel was used. This is consistent with the absorption wavelength of the guanidium salt contained in the cell lysate and the first washing liquid. Thus, it is apparent that in Comparative Example 1, removal of reagent components is insufficient, and thus the purity of the DNA is low with the ratio of the absorbance at a wavelength of 260 nm to the absorbance at a wavelength of 280 nm ($A_{260}/A_{280}$) in the DNA-eluted liquid being about 1.4. Accordingly, when the obtained DNA is subjected to a reaction such as PCR, or used for other analyses, the foreign substances may cause an adverse effect.

On the other hand, in Example 1 where a chemical gel was used, an absorption having a peak around a wavelength of 220 nm as in Comparative Example 1 was not observed, and a DNA-specific absorption peak around a wavelength of 260 nm was clearly observed. The ratio $A_{260}/A_{280}$ in the DNA-eluted liquid in Example 1 was about 1.7. From the result, it is apparent that B/F separability is improved by using a silicone gel so that a high-purity nucleic acid can be easily extracted with a high collection rate.

Example 2

In Example 2, a sample for enzyme immunochemical measurement was prepared using magnetic beads. As the magnetic beads, protein G-coated magnetic particles (Dynabeads Protein G manufactured by Life Technologies, Inc.) were used.

Preparation of Device

For silicon-coating the tube inner wall surface of a capillary made of borosilicate glass (manufactured by HIRSCHMANN LABORGERATE, ringcaps, 200 µl), the tube was filled with a silicon coating agent (Siliconise L-25 Solution manufactured by FUJIRIKA KOGYO K.K.), and the liquid was drawn out 10 minutes later. The capillary was washed with distilled water, and the inside of the tube was dried with nitrogen. Thereafter, the opening at one end of the capillary was closed with a sealing agent (cha-seal). The capillary was loaded through the other opening thereof with 60 µL of a PBST solution (0.02% Tween 20-containing phosphate buffered saline solution) and 20 µL of a silicone gel (KSG-15) in this order from the bottom. This was repeated three times, and finally, the capillary was loaded with 40 µL of a PBST solution. Loading of the gel and solution was performed with the capillary allowed to stand vertically for preventing ingress of bubbles into the tube.

Preparation of Positive Control and Negative Control

To a polypropylene tube having a volume of 1.5 µmL with 100 µL of PBST dispensed therein, 3 µL of magnetic beads suspension was added, and suspended by a vortex mixer. Thereafter, centrifugal separation was performed (1000 rpm, 5 seconds), the tube was allowed to stand on a magnetic stand (manufactured by Life Technologies, Inc., and left standing for 1 minute, and the supernatant was then removed. Thereafter, 100 mL of PBST was added in the tube, and then suspension, centrifugation and removal of the supernatant were performed again.

Subsequently, AP (alkali phosphatase) conjugate Anti-Mouse IgG (manufactured by Promega Corporation) adjusted to have a concentration of 100 pg/μL and 50 μL of 1% BSA-PBS (1% bovine serum albumin-containing phosphate buffered saline solution) solution were added in the tube, and incubated on a tube mixer at room temperature for 15 minutes to prepare a positive control. AP conjugate Anti-Mouse IgG was not added, and only BSA-PBS solution was added to prepare a negative control.

Separation Manipulation

Each of the control liquids together with magnetic beads were introduced into the tubular device through the opening of the device, and by the same magnetic manipulation as in Example 1, the magnet was moved so as to trace the side surface of the container at a speed of 0.5 to 5 mm per second toward the lower end bottom of the device, so that the magnetic beads were manipulated. In each PBST solution, the magnet was attached to and detached from the capillary side surface repeatedly several times for dispersing the magnetic beads in the solution. Finally, the portion of the capillary, which was closed with the cha-seal, was released, and the magnetic beads dispersed in PBST were collected in the tube.

Analysis by ELISA Method

The tube including magnetic beads after manipulation was allowed to stand on a magnetic stand, and left standing for 1 minute, the supernatant was then removed, 100 μL of a PNPP coloring reagent (manufactured by Thermo Co.) was added, and the magnetic beads were suspended by a vortex mixer, followed by carrying out an alkali phosphatase reaction on a tube mixer at room temperature for 15 minutes. Subsequently, 50 μL of reaction stopping agent (2 N aqueous sodium hydroxide solution) was added, and the mixture was mixed, and then subjected to centrifugation (1000 rpm, 5 seconds). The tube was allowed to stand on the magnetic stand, and left standing for 1 minute, 50 μL of the coloring reaction solution was then drawn out, and subjected to absorbance measurement at a wavelength of 405 nm using a spectrophotometer ("BioSpec-nano" manufactured by Shimadzu Corporation).

The absorbances of the positive controls (n=3) were 9.297, 9.254 and 9.311 (average: 9.287). This value was almost as high as that obtained when B/F separation was performed by a conventional method using a general tube (average value of absorbances: 9.213). On the other hand, the absorbances of the negative controls (n=2) were 0.314 and 0.329 (average: 0.322). This value was almost as low as that obtained when B/F separation was performed by a conventional method (average value of absorbances: 0.331).

From the results in Example 2, it has been shown that in a case where particles with AP conjugate Goat anti-Mouse IgG of protein G immobilized thereon are used, it is also possible to perform B/F separation with high efficiency by performing particle manipulation and the immobilization state of the particles are maintained after the particles are caused to pass through a silicone gel. Since foreign components from the gel are not generated, it is possible to detect a target component with high sensitivity in an extremely low background.

From Example 1 and Example 2, it has been confirmed that by manipulation in which particles existing in one water-based liquid are caused to pass through a chemical gel and move to a different water-based liquid, B/F separation can be performed with only the particles moved without being associated with the water-based liquid. It is apparent that in the present invention, a chemical operation can be carried out without causing adverse effects of gel and water-based liquid-derived foreign substances while a target substance stays immobilized on particles. Further, in the method according to the present invention, a plurality of chemical operations can be performed in the closed system in one device without opening and closing a container, so that manipulation is simple and easy. In addition, adverse effects such as contamination can be eliminated.

DESCRIPTION OF REFERENCE SIGNS 50, 52, 53 particle manipulation device
10 to 12 container
21 to 24 gelled medium
31 to 37 water-based liquid
71 to 73 particles
9 magnet
150 particle manipulation device (device for extraction and separation of nucleic acid)
110 container (capillary)
121 to 123 gelled medium (silicone gel)
131, 132 water-based liquid (washing liquid)
133 water-based liquid (eluting liquid)
141 water-based liquid (cell lysate)
171 particles (magnetic beads)

The invention claimed is:
1. A particle manipulation method comprising the steps of:
   moving particles, which exist in a water-based liquid, into a gelled medium that is insoluble or hardly soluble in the water-based liquid; and
   moving the particles to the outside of the gelled medium, wherein
   the particles are capable of selectively immobilizing a specific substance selected from a group consisting of nucleic acids, proteins, sugars, lipids, antibodies, receptors, antigens, ligands and cells, and
   the gelled medium is a silicone gel containing chemically crosslinked organopolysiloxane.
2. The particle manipulation method according to claim 1, wherein
   the gelled medium has a consistency of 340 to 475.
3. The particle manipulation method according to claim 1, wherein the gelled medium further contains an oil solution.
4. The particle manipulation method according to claim 1, wherein
   in movement of the particles into the gelled medium from the water-based liquid and in movement of the particles in the gelled medium, the water-based liquid associated with the particles is separated from the particles.
5. The particle manipulation method according to claim 1, wherein the particles are moved into a different water-based liquid in the step of moving the particles to the outside of the gelled medium.
6. The particle manipulation method according to claim 5, wherein in a device loaded with a plurality of water-based liquids with the gelled medium interposed among the water-based liquids, the step of moving the particle into the gelled medium, and the step of moving the particles into the different water-based liquid are carried out two or more times.

7. The particle manipulation method according to claim 6, wherein at least two of the plurality of water-based liquids have mutually different compositions.

8. The particle manipulation method according to claim 1, wherein the particles are magnetic particles, and moving the particles are performed by magnetic field manipulation.

9. The particle manipulation method according to claim 1, wherein the particles have nucleic acid immobilized thereon, and wherein the nucleic acid is eluted in at least one water-based liquid.

10. The particle manipulation method according to claim 1, wherein an antigen-antibody reaction is performed in at least one water-based liquid.

11. A particle manipulation device comprising: a water-based liquid; a gelled medium that is insoluble or hardly soluble in the water-based liquid; a container for holding the water-based liquid and the gelled medium; and particles to be moved in the container, wherein the particles are capable of selectively immobilizing a specific substance selected from a group consisting of nucleic acids, proteins, sugars, lipids, antibodies, receptors, antigens, ligands and cells, and the gelled medium is a silicone gel containing chemically crosslinked organopolysiloxane.

12. The particle manipulation device according to claim 11, wherein the gelled medium has a consistency of 340 to 475.

13. A particle manipulation device preparation kit for preparing the particle manipulation device of claim 11, comprising: a water-based liquid; a gelled medium that is insoluble or hardly soluble in the water-based liquid; and particles, wherein the particles are capable of selectively immobilizing a specific substance selected from a group consisting of nucleic acids, proteins, sugars, lipids, antibodies, receptors, antigens, ligands and cells, and the gelled medium is a silicone gel containing chemically crosslinked organopolysiloxane.

14. The particle manipulation device preparation kit according to claim 13, wherein the gelled medium has a consistency of 340 to 475.

* * * * *